United States Patent
Euzen et al.

(10) Patent No.: US 10,814,138 B2
(45) Date of Patent: Oct. 27, 2020

(54) ACTIVE IMPLANTABLE MEDICAL DEFIBRILLATION DEVICE

(71) Applicant: SORIN CRM SAS, Clamart (FR)

(72) Inventors: Marie-Anne Euzen, Bièvres (FR); Paola Milpied, Paris (FR)

(73) Assignee: Sorin CRM SAS, Clamart (FR)

( * ) Notice: Subject to any disclaimer, the term of this patent is extended or adjusted under 35 U.S.C. 154(b) by 166 days.

(21) Appl. No.: 16/069,159

(22) PCT Filed: Jan. 9, 2017

(86) PCT No.: PCT/EP2017/050345
§ 371 (c)(1),
(2) Date: Jul. 10, 2018

(87) PCT Pub. No.: WO2017/121702
PCT Pub. Date: Jul. 20, 2017

(65) Prior Publication Data
US 2019/0117990 A1    Apr. 25, 2019

(30) Foreign Application Priority Data

Jan. 11, 2016 (FR) .................................. 16 50194

(51) Int. Cl.
*A61B 5/0464* (2006.01)
*A61N 1/39* (2006.01)
(Continued)

(52) U.S. Cl.
CPC ...... *A61N 1/39622* (2017.08); *A61B 5/04012* (2013.01); *A61B 5/0464* (2013.01);
(Continued)

(58) Field of Classification Search
CPC . A61B 5/04012; A61B 5/0452; A61B 5/0464; A61B 5/7203; A61B 5/7217;
(Continued)

(56) References Cited

U.S. PATENT DOCUMENTS 5,404,880 A    4/1995    Throne
5,797,967 A *  8/1998    KenKnight .......... A61N 1/3962
                                                      607/4
(Continued)

FOREIGN PATENT DOCUMENTS

CN    102831288 A    12/2012
CN    105208928 A    12/2015
EP    2 368 493 A1    9/2011

OTHER PUBLICATIONS

International Search Report and Written Opinion on International Patent Application No. PCT/EP2017/050345 dated Apr. 20, 2017. 12 pages.
(Continued)

*Primary Examiner* — George Manuel
(74) *Attorney, Agent, or Firm* — Foley & Lardner LLP (57) ABSTRACT

This disclosure relates to active implantable medical devices. Some such devices include a pulse generator and at least one detection electrode. A processor of the pulse generator is configured to collect via the detection electrode at least two EGM signals, combine the EGM signals into two time components, and combine the components into a single 2D parametric characteristic representing the cardiac cycle. During a tachyarrhythmia episode, the device stores the consecutive values of the cycle-to-cycle variation in the amplitude of one EGM signal, distributes same into a plurality of classes each corresponding to an amplitude interval, and performs a statistical analysis of the totals for each class so as to output, selectively, on the basis of at least one predetermined criterion applied to the distribution of the amplitude variations into the various classes, an indicator of a suspected extracardiac artifact or an indicator of tachyarrhythmia.

11 Claims, 6 Drawing Sheets

(51) Int. Cl.
*A61B 5/04* (2006.01)
*A61B 5/00* (2006.01)
*A61N 1/02* (2006.01)
*A61N 1/362* (2006.01)
*A61N 1/365* (2006.01)
*A61B 5/0452* (2006.01)

(52) U.S. Cl.
CPC .......... *A61B 5/7203* (2013.01); *A61B 5/7217* (2013.01); *A61N 1/025* (2013.01); *A61N 1/3621* (2013.01); *A61N 1/36507* (2013.01); *A61N 1/3925* (2013.01); *A61N 1/3931* (2013.01); *A61N 1/3987* (2013.01); *A61B 5/0452* (2013.01); *A61B 5/7221* (2013.01); *A61B 5/7264* (2013.01)

(58) Field of Classification Search
CPC .... A61B 5/7221; A61B 5/7264; A61N 1/025; A61N 1/3621; A61N 1/36507; A61N 1/3925; A61N 1/3931; A61N 1/39622; A61N 1/3987
See application file for complete search history.

(56) References Cited

U.S. PATENT DOCUMENTS

| | | |
|---|---|---|
| 2004/0015197 A1 | 1/2004 | Gunderson |
| 2005/0165320 A1 | 7/2005 | Glass et al. |
| 2010/0280567 A1 | 11/2010 | Gunderson |
| 2011/0230776 A1* | 9/2011 | Milpied .............. A61B 5/04011 600/516 |
| 2013/0030481 A1 | 1/2013 | Ghosh et al. |
| 2015/0224321 A1 | 8/2015 | Staeuber et al. |
| 2015/0251012 A1 | 9/2015 | Olson |

OTHER PUBLICATIONS

First Office Action on CN Application No. 201780006222.6 dated May 29, 2020.

* cited by examiner

ACTIVE IMPLANTABLE MEDICAL DEFIBRILLATION DEVICE

CROSS-REFERENCE TO RELATED PATENT APPLICATIONS

This application is a 371 U.S. National Application of International Application No. PCT/EP2017/050345, filed Jan. 9, 2017, which claims the benefit of and priority to French Patent Application No. 1650194, filed Jan. 11, 2016, which is incorporated herein by reference in its entirety.

BACKGROUND

The invention relates to "active implantable medical devices" as defined by Council of the European Communities Directive 90/385/EEC of 20 Jun. 1990, and more precisely to implants for continuously monitoring heart rate and, if necessary, for administering electrical pulses to the heart for stimulation, resynchronization, and/or defibrillation, in the event heart arrhythmia is detected by the device.

The invention relates more specifically to equipment making it possible to administer antitachycardia therapies to the heart, involving controlled application of defibrillation shocks (high-energy electric pulses designed to terminate tachyarrhythmia) and/or therapies by high-frequency stimulation of the type known as "antitachycardia pacing" or "ATP".

A difficulty lies in the fact that such devices are sensitive to detecting external signals of non-cardiac origin that are due to problems related to the lead, to electromagnetic interference, to sensing of myopotentials, etc., such phenomena being referred to below under the generic term of "noise".

Such phenomena might deceive the device, thereby giving rise to very serious consequences, e.g. by wrongly inhibiting anti-bradycardia stimulations or indeed, conversely, by causing inappropriate defibrillation shocks to be administered, due to "oversensing" of extracardiac signals that bear no relation to ventricular tachyarrhythmias.

Applying a defibrillation shock to a conscious patient is extremely painful and frightening, the energies applied being far beyond the pain threshold. In addition, applying a defibrillation shock is not without side effects on the heart rate, i.e. on the cardiac rhythm (risk of occurrence of secondary disorders), on the functional integrity of the myocardium, and in general on the physiological equilibrium of the patient. It is therefore important not to administer such shocks inappropriately.

Various techniques have been proposed for filtering or for discriminating extracardiac noise phenomena a priori, before ventricular sensing, or for analyzing the collected signal a posteriori, in order to determine whether or not it is potentially interfered with by the noise, and, if necessary, in order to modify operation of the device when noise is suspected.

Thus, Document EP 2 368 493 A1 (Sorin CRM) proposes a method of detecting and of eliminating ventricular noise, that method being based on two-dimensional (2D) analysis of two endocardial electrogram (EGM) signals that are collected concurrently on respective ones of two distinct channels. In that document, the two distinct channels are channels coming from the same cavity, namely the right ventricle in that document, but in general the technique may also be implemented using EGMs coming from two different cavities.

The two different EGM channels may, in particular, respectively be that of a unipolar signal (far-field signal collected between the housing and a distal or a proximal electrode) and that of a bipolar signal (near-field signal collected between a distal electrode and a proximal electrode). The two-dimensional analysis is performed over a "cardiac loop" or "vectogram" (VGM), which is a representation in two-dimensional space of one of the two signals relative to the other, each heart beat or significant fraction of a beat then being represented by its vectogram in the plane thus defined.

More specifically, the analysis method consists in describing the VGM by a descriptor parameter of the intrinsic morphology of the VGM, typically the mean angle formed by the consecutive velocity vectors along the path of the loop of the VGM. Analysis of that morphological descriptor then makes it possible to determine whether the current beat is of cardiac origin or whether it is noise. The choice of that particular descriptor is based on the assumption that, for a genuine cardiac complex, two consecutive vectors should not change direction too much, while, for noise, two consecutive velocity vectors can go in widely differing directions, or indeed in opposite directions.

Various actions can be taken depending on whether the cycles are valid or invalid, in particular:
 deleting markers that correspond to invalid, noisy cycles;
 possibly modifying the sensitivity of the detection circuits or some other parameter that acts on the sensing, i.e. on the detection;
 inhibiting or delaying a therapy;
 changing the marking for identifying tachyarrhythmia episodes;
 lengthening the refractory periods; and/or
 deleting the invalid episodes stored in a memory.

Clinical trials show that implementing the method described by EP 2 368 493 A1, with a descriptor corresponding to the mean angle between two consecutive velocity vectors procures a detection specificity close to 100%.

However, the detection sensitivity is not optimum, and depends on the origin of the noise: thus, when the origin is a lead breaking, and since the noise is present in both of the signals used for constructing the VGM, the vectogram progresses approximately continuously and the variation in the angle of the velocity vector might not be sufficient to come to the conclusion that noise is present, and/or that variation might be large only over a small number of cycles, not making it possible to come to a conclusion, and thus not making it possible to inhibit a therapy and/or to alert a physician.

SUMMARY

An object of the present invention is to remedy that difficulty, by proposing an improvement to the above method that is disclosed by above-mentioned Document EP 2 368 493 A1, which improvement enables the sensitivity of the noise detection to be increased with total safety, while also avoiding the risks of oversensing, in particular due to a lead breaking, so the actions that are required as a function of the origin of the noise can be taken with total safety and without delay.

A subsidiary object of the invention is, as explained below, in the absence of detected noise, i.e. in a situation with a valid cycle, to make it possible to analyze the tachyarrhythmia episode by distinguishing between monomorphic tachyarrhythmia and polymorphic tachyarrhythmia.

More specifically, the invention provides a device that, in a manner known per se, comprises:
- means for collecting depolarization signals of ventricular origin, which means comprise:
  - means suitable for collecting at least two different endocardial electrogram, EGM, signals during the same cardiac cycle, concurrently on respective ones of distinct channels, and for deriving from said signals at least two respective distinct time components;
  - means suitable for combining the at least two time components into at least one parametric 2D characteristic curve representative of said cardiac cycle, on the basis of the variations of one of the time components as a function of the other time component;
  - means suitable for deriving from the 2D characteristic curve a geometrical descriptor representative of the 2D characteristic curve; and
  - means suitable for determining the variation of said geometrical descriptor over said cardiac cycle;
- means for applying a defibrillation shock or antitachycardia pacing stimulation pulses;
- means for detecting ventricular tachyarrhythmia episodes; and
- means for detecting artifacts of extracardiac origin, which means are suitable for comparing said variation in the geometrical descriptor with a predetermined threshold, and for inhibiting the means for applying a defibrillation shock or antitachycardia pacing stimulation pulses when said variation in the geometrical descriptor is greater than said predetermined threshold.

In a manner characteristic of the invention, the means for detecting artifacts of extracardiac origin comprise means that, at each cycle of a detected tachyarrhythmia episode and when the variation in the geometrical descriptor is not greater than the predetermined threshold, are suitable for:
- measuring and storing in a memory the successive values of the cycle-to-cycle variation in the amplitude of the at least one of said EGM signals;
- distributing into a plurality of classes said amplitude variation values stored the memory, each class corresponding to an amplitude interval; and
- statistically analyzing the size of each class in such a manner that an indicator of suspicion of an artifact of extracardiac origin or an indicator of type of tachyarrhythmia is delivered selectively as a function of at least one predetermined criterion applied to the distribution of the amplitude variations in the various classes.

According to various advantageous subsidiary characteristics:
- the geometrical descriptor is the mean angle of the velocity vector tangential to the 2D characteristic curve, considered at a plurality of respective points of said characteristic curve;
- the various classes correspond to contiguous and equal amplitude intervals;
- the predetermined criterion is the presence of two non-empty classes separated by a predetermined interval of consecutive empty classes, and the indicator is an indicator of suspicion of an artifact by noise of extraventricular origin, it being possible in particular for the predetermined interval to be an interval corresponding to a difference between non-empty classes of at least 10 millivolts (mV);
- the predetermined criterion is the presence of at least one non-empty class corresponding to an amplitude interval greater than a given first limit value, and the indicator is an indicator of suspicion of an artifact by breakage of a lead, it being possible in particular for the said first limit value to be at least 20 mV;
- the said predetermined criterion is the fact that, in the absence of detection of an artifact by the means for detecting artifacts of extracardiac origin, all of the non-empty classes are classes corresponding to amplitude intervals less than a given second limit value that is less than said first limit value, and the indicator is an indicator of monomorphic tachyarrhythmia, it being possible in particular for said second limit value to be at least 2 mV;
- the said predetermined criterion is the fact that, in the absence of detection of an artifact by the means for detecting artifacts of extracardiac origin, all of the non-empty classes are classes corresponding to amplitude intervals less than a given third limit value that is greater than said second limit value and less than said first limit value, and the indicator is an indicator of polymorphic tachyarrhythmia, it being possible in particular for said third value to be at least 5 mV.

BRIEF DESCRIPTION OF THE DRAWINGS

An embodiment of the present invention is described below with reference to the accompanying drawings, in which like references designate identical or functionally similar elements from one figure to another, and in which.

DETAILED DESCRIPTION

An embodiment of the device of the invention is described below.

As regards its software aspects, the invention can be implemented by appropriate programming of the control software of a known device comprising means for acquiring signals provided by endocardial leads and/or by one or more implanted sensors, and means for applying an antitachycardia therapy (defibrillation shock and/or ATP stimulation).

The invention may, in particular, be applied to implantable devices such as those belonging to the Paradym or Platinum families of devices that are produced and marketed by Sorin CRM, Clamart, France.

Such a device has a programmable microprocessor and comprises circuits for receiving, shaping, and processing the electrical signals collected by implanted electrodes, and for delivering stimulation and defibrillation pulses to said electrodes. It is possible to transmit software to it by telemetry, which software is kept in a memory and is executed for implementing the functions of the invention that are described below. Adapting such equipment to implementing the functions of the invention is within the capacities of the person skilled in the art, and is not described in detail.

The method of the invention is implemented mainly by software means, using suitable algorithms executed by a microcontroller or a signal digital processor. To make the description clearer, the various types of processing applied are broken down and represented diagrammatically by a certain number of distinct functional blocks shown in the form of interconnected circuits, but this representation is given merely by way of illustration, said circuits comprising common elements and corresponding, in practice, to a plurality of functions generally executed by a common piece of software.

Figure 1:
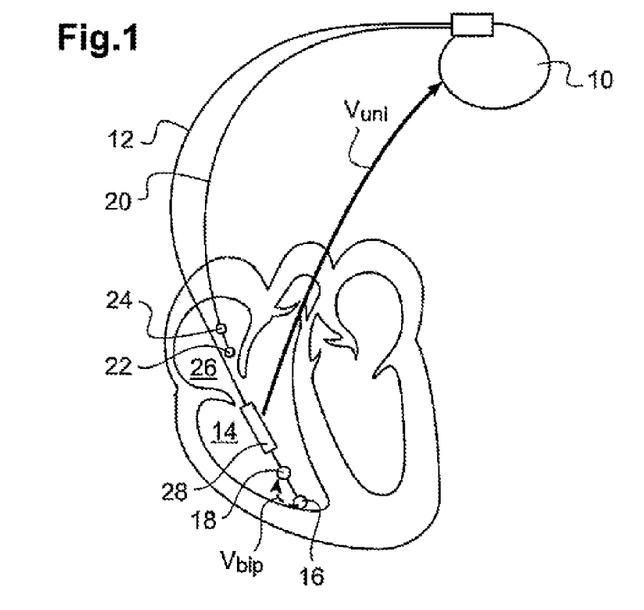
FIG. 1 is an overall view of a stimulation/defibrillation device with its generator and a lead implanted in the right heart.

FIG. 1 shows a typical "dual chamber" stimulation or pacing configuration in which a pulse generator 10 is associated with a first lead 12 implanted in the right ventricle 14. The head of this lead has two electrodes, namely a distal electrode (tip electrode) 16 and a proximal electrode (ring electrode) 18. An optional second lead 20 is provided with distal and proximal detection atrial electrodes, respectively 22 and 24, situated at the right atrium 26 for detecting signals therein and, when appropriate, for applying atrial stimulation.

The right ventricular lead 12 is also provided with a ventricular coil 28 forming a defibrillation electrode and also making it possible to collect an endocardial signal (it then being possible for this coil to be used in place of the ring proximal electrode 18).

If the device also has ventricular resynchronization functions (Cardiac Resynchronization Therapy or "CRT"), a lead for stimulating the left ventricle is also provided, typically a lead inserted via the coronary venous system.

Firstly, it is necessary to combine two endocardial electrogram signals collected from the patient in spontaneous rhythm, in particular signals coming from the same ventricular cavity, e.g. from the right ventricle.

The EGMs collected for this purpose in the right ventricle may, for example, comprise (see FIG. 1):

a right ventricular component Vbip, derived from a bipolar near-field EGM signal collected between the distal electrode 16 and the proximal electrode 18 of the right ventricular lead 12; and another right ventricular component Vuni, derived from a unipolar far-field EGM signal collected between the defibrillation coil 28 of the right ventricular lead 12 and the metal housing of the generator 10.

Other configurations may be used, on the basis of signals of the far-field type (e.g. between one of the electrodes 16 and 18 and the housing 10) and of the near-field type (between two electrodes of the same ventricular lead).

Figure 2:
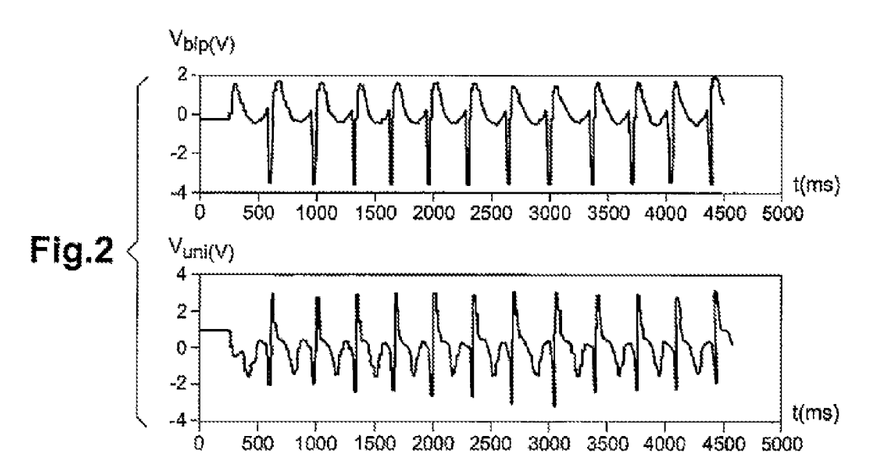
FIG. 2 is an example of EGM signals obtained on respective ones of the bipolar ventricular and unipolar ventricular channels of one of the leads in FIG. 1.

FIG. 2 shows an example of plots for EGMs Vbip and Vuni observed respectively on the ventricular bipolar channel and on the ventricular unipolar channel of the configuration of FIG. 1.

These two signals, namely the bipolar signal and the unipolar signal, are combined into a single characteristic curve of the "cardiac loop" or "vectogram" (VGM) type, which is a representation in two dimensional space of one of the two EGM signals (in ordinate) relative to the other (in abscissa). Each cardiac cycle is then represented by a vectogram in the plane {Vbip, Vuni} thus defined, namely a vectogram of geometrical shape (shape of the curve) that thus disregards the time dimension, which is involved only as a parameter describing the way in which the curve is travelled.

It should be emphasized that this "vectogram" (VGM), which is obtained on the basis of electrogram (EGM) signals coming from intracardial leads, should not be confused with the "vectorcardiogram" (VCG), which is obtained on the basis of electrocardiogram (ECG) signals coming from external electrodes placed on the thorax of the patient.

It should also be noted that the "two-dimensional" or "2D" analysis mentioned herein should not be understood to be limiting per se. The invention is equally applicable to analysis in multi-dimensional space of a higher order (three-dimensional (3D) or more), by extrapolating the teaching of the present description to a situation in which EGM signals coming from the same cavity are collected simultaneously on three or more channels.

Figure 3:
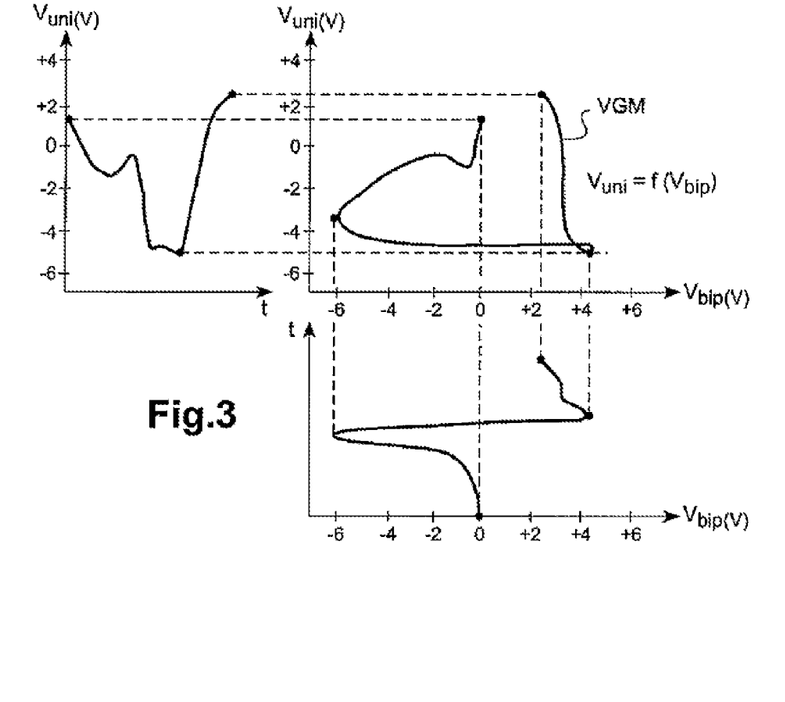
FIG. 3 shows how the bipolar and unipolar signals collected from the same ventricular cavity are combined to construct a two-dimensional characteristic curve of the vectogram type, independent of time.

As shown in FIG. 3, the EGM signals Vuni(t) and Vbip(t) that are collected are sampled, and the successive samples of the two components are stored in a memory and then mutually combined to produce a parametric curve (the VGM characteristic curve) of the type VGM=(Vbip(t), Vuni(t)) or {x=Vbip(t), y=Vuni(t)}.

In other words, this curve is a curve that is parameterized by time, and plotted on the basis of variations in one of the time components (Vuni) as a function of the other one (Vbip). It constitutes a vectogram (VGM) representative of the cardiac cycle to be analyzed, and is also referred to as a "parametric 2D characteristic curve". Graphically, it is in the form of a loop, time appearing only in the manner in which the loop is travelled over the duration of the cycle.

Figure 4:
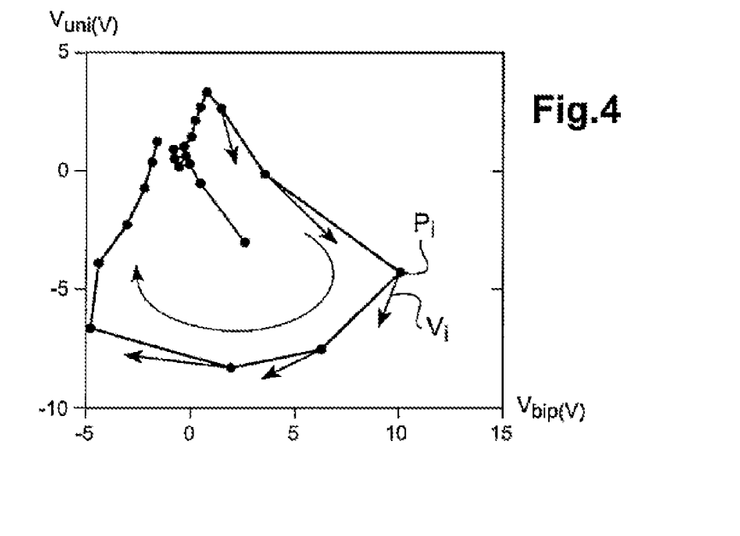
FIG. 4 shows an example of a sampled vectogram obtained for a cardiac cycle sampled at 128 hertz (Hz), with the velocity vectors being shown at various successive points.

In practice, as shown in FIG. 4, the sampling produces a VGM in the form of an open polygon in which each vertex corresponds to a point of sampling of the measurement of the signal Vuni and Vbip of the EGM. In the example of FIG. 4, the sampling is effected at a frequency of 128 Hz, which gives about 11 measurement points for a time interval of 80 milliseconds (ms), thereby producing as many values, which can be stored in a memory for analysis.

FIG. 4 also shows the appearance of the velocity vector Vi, at various successive points Pi, of the VGM, for a sampling frequency of 128 Hz. At any given point, velocity constitutes vector data (velocity being defined by its direction and by its norm or magnitude), and the velocity vector can be computed at each point of the VGM on the basis of a discrete filter that approximates the first derivatives dVbip(t)/dt et dVuni(t)/dt that, for a sampled characteristic curve, can be computed on the basis of the preceding point and of the following point on the curve.

The VGM characteristic curve that is collected is stored in a memory in the form of a series of descriptor parameters based on the velocity vectors at each point of the curve, and including the norm of the velocity vector and the direction of said velocity vector, i.e. the angle it makes relative to the axis of the abscissae of the VGM.

In this context, the specific aspects of the invention are described below.

The underlying idea of the present invention consists essentially, during a tachyarrhythmia episode, in combining:

analysis of the morphological descriptor of the VGM (i.e. the variation in the mean angle between two consecutive velocity vectors V, which variation is referred to below as "$\Delta V$"), as taught by above-mentioned Document EP 2 368 493 A1; with an analysis of the variation in the amplitude A (variation referred to below as "$\Delta A$") of one of the two EGM signals that is used for the ventricular detection, and preferably the bipolar EGM, monitoring of the cycle-to-cycle amplitude variation taking place by computing the difference $\Delta A$ between the "peak-to-peak" amplitude A of the current beat and that of the preceding beat.

For each current beat, a value is computed for the mean angle between two consecutive velocity vectors, thereby constituting a descriptor referred to below as $\Delta V$.

This descriptor $\Delta V$ reflects the progress of the vectogram for a given cycle, which progress may be relatively continuous ($\Delta V$ is then less than a given threshold) for a genuine cardiac complex, or, conversely, be much more erratic (leading to a much higher value for the descriptor $\Delta V$).

In the latter situation, an amplitude difference $\Delta A$ that is too large between two consecutive cycles (e.g. $\Delta A > 20$ mV) is considered as being non-physiological, making it possible to conclude that there is a problem with a lead, and resulting in administering of a therapy being suspended at least temporarily.

More specifically, in order to analyze the parameter $\Delta A$ finely, the successive values of the amplitude difference $\Delta A$ between a current cycle and the preceding cycle are stored in a memory over a predetermined number of cycles, and the stored values are then distributed into a plurality of predefined classes, each class corresponding to a given amplitude interval.

The various classes $C_i$ preferably correspond to contiguous and equal amplitude intervals $\Delta A$.

For example, if classes are chosen that correspond to an interval of 1 mV, then the classes comprise:

a first class C1 grouping together the values for $\Delta A$ lying in the range 0 mV to 1 mV;

a second class C2 grouping together the values for $\Delta A$ lying in the range 1 mV to 2 mV;

a third class C3 grouping together the values for $\Delta A$ lying in the range 2 mV to 3 mV;

and so on.

For the remainder of the analysis, it is necessary to keep in the memory only the definitions of the classes $C_i$ and the number $N_i$ of cardiac cycles for which the value $\Delta A$ corresponds to the class in question $C_i$.

The distribution of the values $\Delta A$ between the various classes can be represented visually in the form of histograms such as those shown in the examples of FIGS. 6a, 6b, 7a and 7b, and described in more detail below.

The distribution of the values for $\Delta A$, and thus the profile of the histogram, makes it possible, in accordance with the invention, to produce additional information:

i) either on any presence of external noise or on a situation in which a lead has broken;

ii) or, in the absence of noise, on the particular nature of the tachyarrhythmia-monomorphic or polymorphic.

With reference, in particular, to the flow chart of FIG. 8, it is explained in more detail below how this distribution of the $\Delta A$ values is analyzed so as to derive this specific additional information therefrom.

Figure 5:
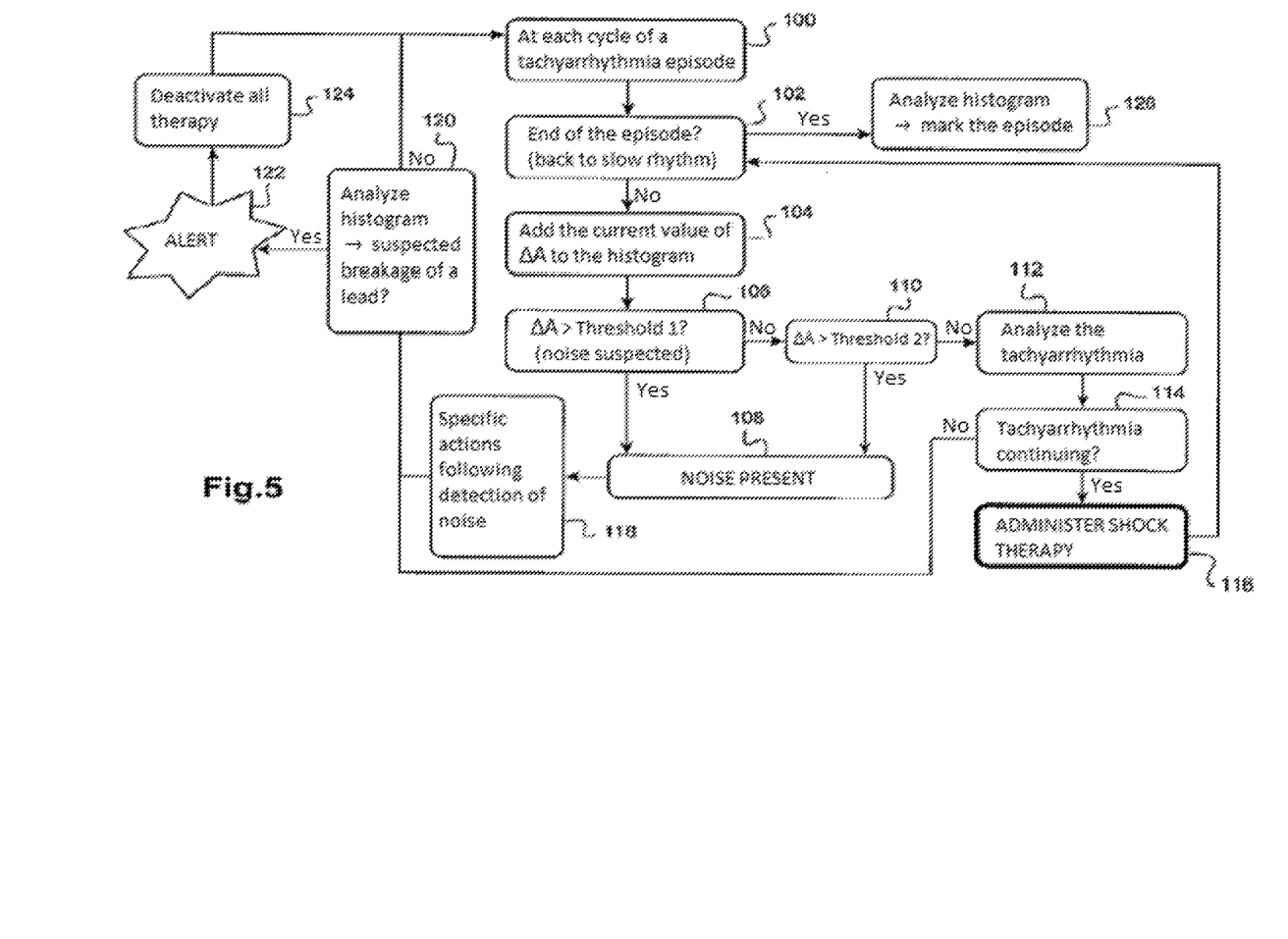
FIG. 5 diagrammatically shows the various steps in implementing the method of the invention for detecting and managing noise.

FIG. 5 diagrammatically shows the various steps in implementing the method of the invention.

The various tests and actions of this method are executed when the patient is in a situation of tachyarrhythmia, at each cycle of the episode (block 100).

The first step consists in detecting any return of the cardiac rhythm to the slow sinus rhythm, which would indicate the end of the tachyarrhythmia episode (block 102).

If the answer to that test is negative, i.e. if the patient is still in a situation of tachyarrhythmia, the difference in amplitude $\Delta A$ between the current cycle and the preceding cycle is computed and classified, i.e. the corresponding class $C_i$ of the histogram is incremented by one (block 104).

The next step consists, in a manner known per se (in particular from above-mentioned Document EP 2 368 493 A1), in evaluating the variation $\Delta V$ in the mean angle of the velocity vector for the current VGM, and in comparing that variation $\Delta V$ with a first threshold, Threshold 1 (block 106).

An affirmative answer, revealing a relatively erratic path of the vectogram during the cardiac cycle, is considered to be an indication that noise is present, and a specific indicator is positioned (block 108). Otherwise, and in a manner characteristic of the invention, it is not concluded that noise is absent, but rather a second test is performed, based on the amplitude difference $\Delta A$ between the current cycle and the preceding cycle, that value of $\Delta A$ being compared with a second threshold (Threshold 2) (block 110):

if the amplitude variation is greater than the threshold, then presence of noise is confirmed (block 108);

otherwise, it is considered that a non-noisy cardiac signal is present that can be analyzed by applying a usual arrhythmia classification algorithm (block 112), e.g. the algorithm Parad that is used in devices designed by Sorin CRM, and that is described EP 0 838 235 A1 (ELA Medical).

If the analysis of the tachyarrhythmia reveals that said tachyarrhythmia is continuing (block 114), then it is appropriate (optionally if other conditions are satisfied after analyzing the arrhythmia) to apply a therapy, typically by applying a defibrillation shock (block 116). Then, the process loops back to block 102 to check whether the applied therapy has indeed terminated the tachyarrhythmia episode.

If persistent tachyarrhythmia is not detected in block 114, the histogram is then analyzed (block 120, described below).

If appropriate, a noise presence indicator has been positioned in step 108, and the device then takes a certain number of specific actions, conducive to detecting noise. Among those actions, mention can be made of the following:

adjusting the sensitivity;

inhibiting the therapy; and possibly administering a ventricular stimulation.

More specifically regarding the latter action, it should be noted that if the patient is dependent (atrioventricular block) and if the device detects noise, the device does not stimulate at the correct time, thereby generating a ventricular pause that can more or less long. Stimulation at a vulnerable instant (in particular during the repolarization T wave) is more dangerous than a ventricular pause; but conversely, in certain situations, if a sinus rhythm is absent, a stimulation is necessary and safe.

To identify whether or not such a rhythm is present (whether or not a heartbeat is present) by means of the right ventricular EGM signal only, it is necessary for the amplitude of the noise to be small.

If the cycle has been considered to be a noisy cycle (presence of noise indicated in block 108):

if the peak-to-peak amplitude A of the current beat is less than a given threshold (e.g. less than 1 mV, or less than a fraction of the mean amplitude in sinus rhythm), then the escape interval of the device is not reset, and a ventricular stimulation is applied at the end of said interval;

conversely, if said amplitude A is greater than the threshold, then the escape interval is reset, so as to avoid stimulation at an inappropriate time that could be a factor triggering an arrhythmia.

Signals other than the bipolar right ventricular EGM signal may be used, where applicable, for determining whether stimulation is necessary in the event noise is detected. Thus:

for patients equipped with a resynchronization device having a left ventricular lead, it may be decided not to reset the ventricular escape interval so long as no depolarization of the left ventricle is detected;

for patients having a lead provided with an implanted endocardial acceleration (EA) sensor, e.g. a lead provided with an accelerator integrated into the end of the lead, the ventricular escape interval is not reset so long as no EA component is detected, i.e. so long as no component revealing a mechanical contraction of the ventricle is detected.

Once the specific actions in the presence of noise have been taken (block 118) or, in the absence of noise, after it has been confirmed that the tachyarrhythmia episode is continuing (block 114), in a manner characteristic of the invention, the process effects an analysis of the histogram of the ΔA values (block 120), in particular in order to discriminate between genuine external noise and a possible breakage of a lead. If a lead breakage is established, then an alert is generated (block 122) and all therapy is deactivated (block 124) for safety reasons.

Figure 6A:
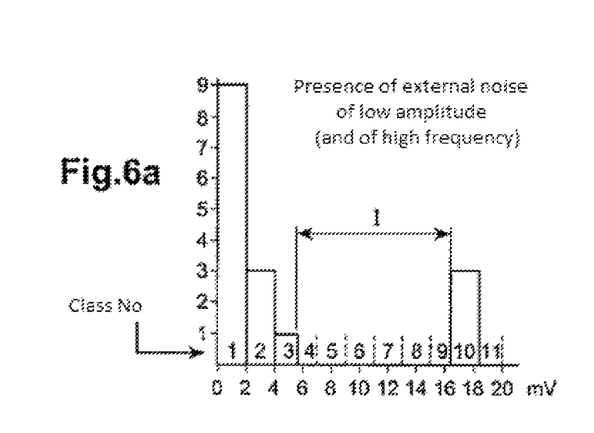
FIGS. 6a and 6b show histograms obtained by implementing the method of the invention, in various situations in which external noise is established.
Figure 6B:
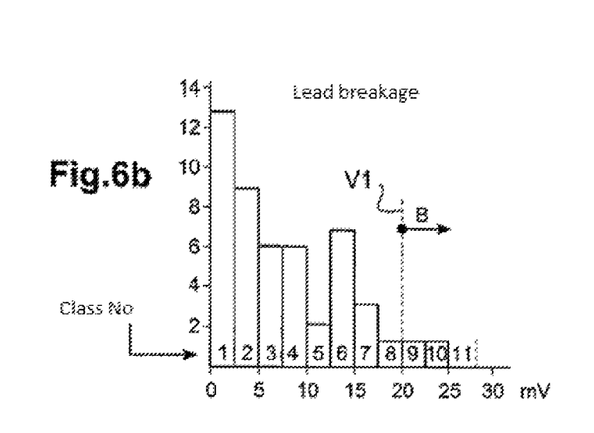

FIGS. 6a and 6b show two examples of histograms obtained when the device suspects the presence of noise (block 108), solely on the basis of the analyses of the parameters ΔV and ΔA.

This situation can actually cover two different cases, shown respectively by FIGS. 6a and 6b.

In the situation in FIG. 6a, external noise of low amplitude and of high frequency is genuinely present, as expressed on the histogram by the presence of two clearly distinct groups (classes 1 to 3 and class 10) separated by an interval I greater than a given threshold, e.g. two groups mutually separated by more than I=10 mV.

In this example, each class corresponds to an interval ΔA of about 1.8 mV and two clearly distinct groups can be observed on the histogram, one situated approximately in the range 0 mV to 5 mV (classes 1 to 3, corresponding to the consecutive noisy cycles) and the other around 18 mV (class 10, corresponding to going from a normal cardiac cycle to external noise of low amplitude and of high frequency, and vice versa).

In the situation in FIG. 6b, the distribution of the various classes is much more random and it can be noted that non-empty classes are present in an upper region B corresponding to cycle-to-cycle variability greater than the threshold V1, e.g. V1=20 mV.

In this example, each class corresponds to an interval ΔA of 2.5 mV. The presence of consecutive beats having very large differences in amplitude ΔA (classes 9 and 10 not empty, for values greater than 20 mV) reveals a serious anomaly, very probably resulting from a lead breaking.

Figure 7A:
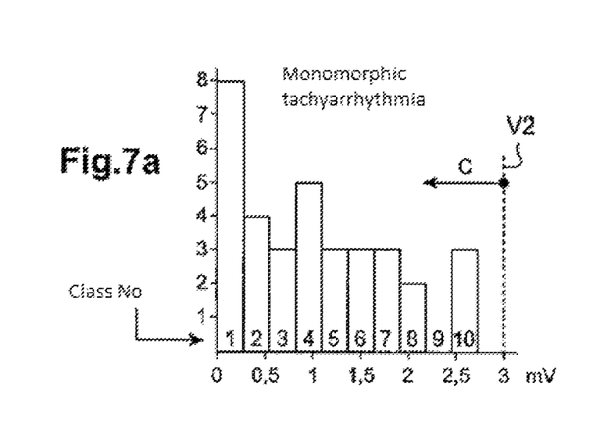
FIGS. 7a and 7b show histograms obtained by implementing the method of the invention, in various tachyarrhythmia situations in which no external noise is detected.
Figure 7B:
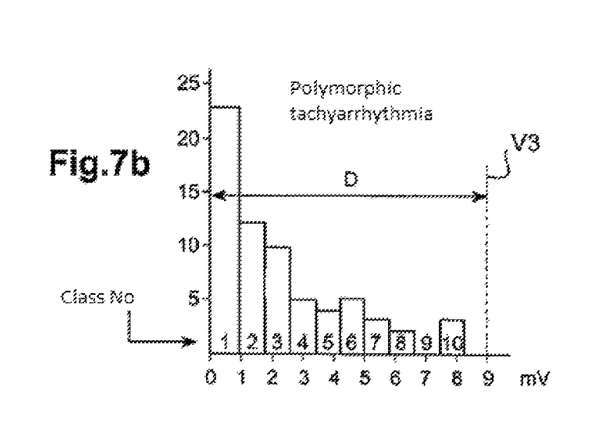

FIGS. 7a and 7b show two examples of distribution of the classes of the histogram that are analyzed in block 120, in the situation in which the device has not detected any noise and in which persistent tachyarrhythmia is present as established in block 114.

In a manner characteristic of the invention, but in subsidiary manner, it is possible to determine whether the tachyarrhythmia is monomorphic or polymorphic, by analyzing the histogram of the ΔA values.

In the example of FIG. 7a, each class corresponds to an interval ΔA of 0.275 mV. The non-empty classes (classes 1 to 8 and 10) are all situated within a region C corresponding to a value less than a given threshold V2, e.g. V2=3 mV, and it can be concluded that the tachyarrhythmia is monomorphic.

In the example of FIG. 7b, each class corresponds to an interval ΔA of 0.825 mV. The non-empty classes are all distributed over a range D extending to a maximum threshold V3 (where V2<V3<V1), e.g. V3=9 mV, and it can be concluded that the tachyarrhythmia is polymorphic.

Figure 8:
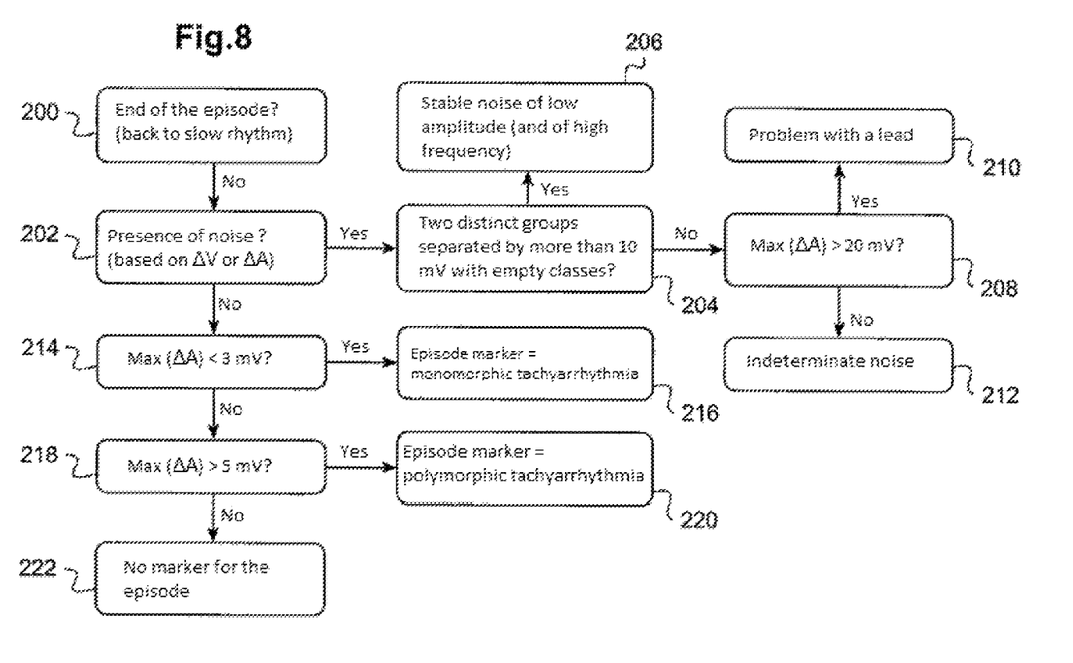
FIG. 8 diagrammatically shows the various steps in analyzing the arrhythmia profiles based on histograms such as those shown in FIG. 5 and FIG. 6.

FIG. 8 shows an example of a flow chart for analyzing the distribution of the various ΔA values in the classes of the histogram that is implemented only if the tachyarrhythmia episode continues (block 200, corresponding to the test 102 of FIG. 5).

Any presence of noise is detected in the manner explained above (block 202, corresponding to the blocks 106 and 110 of FIG. 5).

In the event noise is suspected, a search is made to determine whether the histogram comprises two distinct groups separated by an interval I greater than a predetermined value, e.g. separated by more than 10 mV with empty classes (block 204). If it does comprise such groups, that indicates the presence of stable noise, of low amplitude (block 206).

To highlight such groups, the algorithm analyzes the number of values in each class. If a plurality of consecutive classes, e.g. ten classes, are empty and are situated in a domain less than a maximum value Max(ΔA), then it is possible to confirm the presence of distinct groups in the histogram, revealing stable noise of low amplitude.

In addition, if the sum of the Ni values of the first group (the group in which the amplitude values are the lowest) is at least x times, e.g. x=3 times, greater than the sum of the Ni values of the second group (having the highest interval values, corresponding to going from the noisy zone to a normal cardiac cycle and vice versa), then it can be concluded that stable noise of low amplitude and of high frequency is present.

If, at block 204, the analysis did not make it possible to observe two clearly distinct groups in the histogram then it is examined whether the highest non-empty class Max(ΔA) is greater than the threshold V1, e.g. V1=20 mV (block 208). If it is, then a problem with a lead is probably present (block 210); otherwise, a lead breakage is not confirmed, and it is considered that noise of an indeterminate nature is present (block 212).

If, in step 202, it is considered that no noise is present, then the algorithm seeks to determine whether the highest non-empty class Max(ΔA) is less than the threshold V2 (block 214).

If it is, it is considered that monomorphic tachyarrhythmia is present (block 216), and the episode is marked accordingly.

If it is not, another test is performed relative to the threshold V3 (block 218): if Max(ΔA) exceeds that threshold, polymorphic tachycardia is present (block 220) and the episode is marked accordingly. Otherwise (block 202), it is not possible to come to a conclusion, and the episode is not marked.

Figure 9:
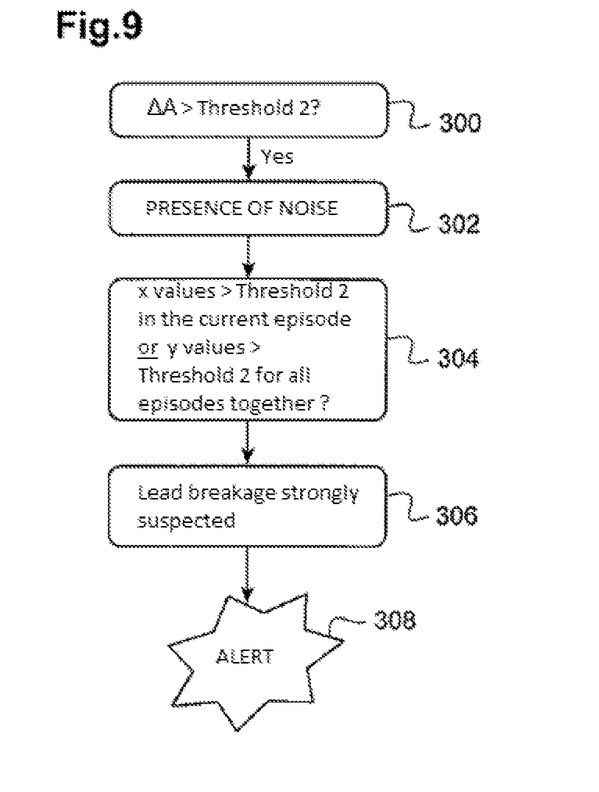
FIG. 9 diagrammatically shows the various steps in analysis leading to conclude that a lead has broken.

FIG. 9 diagrammatically shows the various steps in analysis leading to conclude that a lead has broken, corresponding to block 122 in FIG. 5.

In addition to comparing the amplitude difference ΔA with the threshold Threshold 2, e. g. with the threshold of 20 mV (block 300, corresponding to block 110 in FIG. 5), if noise is suspected (block 302, corresponding to block 108 in FIG. 5), then before triggering the alert, additional criteria are applied. Thus, it is only if x values for ΔA are found that are greater than Threshold 2 in the current episode, or if y values for ΔA are found that are greater than Threshold 2 for all of the episodes together, that it is considered that there is a genuine suspicion of a lead breakage (block 306) and that an alert is triggered (block 308).

The invention claimed is:

1. An active implantable medical device, comprising:
a detection electrode; and
a pulse generator comprising a memory having instructions stored thereon and a processor configured to execute the instructions to deliver a defibrillation shock or antitachycardia pacing stimulation pulses to at least one ventricle of a patient carrying the device, the pulse generator configured to collect depolarization signals of ventricular origin, the pulse generator configured to:
collect at least two different endocardial electrogram signals during the same cardiac cycle, concurrently on respective ones of distinct channels, and derive from said signals at least two respective distinct time components;
combine the at least two time components into at least one parametric 2D characteristic curve representative of said cardiac cycle, on the basis of the variations of one of the time components as a function of the other time component;
derive from the 2D characteristic curve a geometrical descriptor representative of the 2D characteristic curve;
determine the variation of said geometrical descriptor over said cardiac cycle;
detect ventricular tachyarrhythmia episodes;
detect artifacts of extracardiac origin;
compare said variation in the geometrical descriptor with a predetermined threshold;
inhibit the application of a defibrillation shock or antitachycardia pacing stimulation pulses when said variation in the geometrical descriptor is greater than said predetermined threshold; and
at each cycle of a detected tachyarrhythmia episode and when the variation in the geometrical descriptor is not greater than the predetermined threshold:
measure and store in a memory the successive values of the cycle-to-cycle variation in the amplitude of the at least one of said EGM signals;
distribute into a plurality of classes said amplitude variation values stored the memory, each class corresponding to an amplitude interval; and
statistically analyze the size of each class in such a manner that an indicator of suspicion of an artifact of extracardiac origin or an indicator of type of tachyarrhythmia is delivered selectively as a function of at least one predetermined criterion applied to the distribution of the amplitude variations in the various classes.

2. The device of claim 1, wherein the geometrical descriptor is the mean angle of the velocity vector tangential to the 2D characteristic curve, considered at a plurality of respective points of said characteristic curve.

3. The device of claim 1, wherein the classes correspond to contiguous and equal amplitude intervals.

4. The device of claim 1, wherein:
the said predetermined criterion is the presence of two non-empty classes separated by a predetermined interval of consecutive empty classes, and
the indicator is an indicator of suspicion of an artifact by noise of extraventricular origin.

5. The device of claim 4, in which the predetermined interval is an interval corresponding to a difference between non-empty classes of at least 10 mV.

6. The device of claim 1, wherein:
the said predetermined criterion is the presence of at least one non-empty class corresponding to an amplitude interval greater than a given first limit value; and
the indicator is an indicator of suspicion of an artifact by breakage of a lead.

7. The device of claim 6, wherein the said first limit value is at least 20 mV.

8. The device of claim 6, wherein:
the said predetermined criterion is the fact that, in the absence of detection of an artifact by the pulse generator, all of the non-empty classes are classes corresponding to amplitude intervals less than a given second limit value that is less than said first limit value; and
the indicator is an indicator of monomorphic tachyarrhythmia.

9. The device of claim 8, wherein the said second limit value is at least 2 mV.

10. The device of claim 8, wherein:
the said predetermined criterion is the fact that, in the absence of detection of an artifact by the pulse generator all of the non-empty classes are classes corresponding to amplitude intervals less than a given third limit value that is greater than said second limit value and less than said first limit value; and
the indicator is an indicator of polymorphic tachyarrhythmia.

11. The device of claim 10, wherein the said third limit value is at least 5 mV.

* * * * *